US00PP28896P2

(12) United States Plant Patent
Ault

(10) Patent No.: US PP28,896 P2
(45) Date of Patent: Jan. 23, 2018

(54) ***PHLOX* PLANT NAMED 'PLUMTASTIC'**

(50) Latin Name: ***Phlox subulata*×*Phlox kelseyi***
Varietal Denomination: Plumtastic

(71) Applicant: James Robert Ault, Libertyville, IL (US)

(72) Inventor: James Robert Ault, Libertyville, IL (US)

(73) Assignee: CHICAGO LAND GROWS, INC, Glencoe, IL (US)

( * ) Notice: Subject to any disclaimer, the term of this patent is extended or adjusted under 35 U.S.C. 154(b) by 0 days.

(21) Appl. No.: 15/330,385

(22) Filed: Sep. 13, 2016

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Annette Para
(74) *Attorney, Agent, or Firm* — Penny J. Aguirre

(57) ABSTRACT

A new cultivar of *Phlox* plant named, 'Plumtastic', that is characterized by its low dense groundcover habit, its petals that overlap for one-half to three-quarters of their length, its flowers that emerge light rose pink in color, ageing to a medium and then dark rose to red-violet color, its flowers that emerge with a large, distinct center eye that is white in color and fills with pigment as the flowers age, its small petal striae that form two distinct dark violet lines at the base of each petal lobe and persist for the life of the flower, and its flowers that cover 90% of the plant at peak bloom.

2 Drawing Sheets

Botanical classification: *Phlox subulata*×*Phlox kelseyi*.
Cultivar designation: 'Plumtastic'.

BACKGROUND OF THE INVENTION

The present invention relates to a new and distinct cultivar of *Phlox* plant, botanically an interspecific hybrid known as *Phlox* 'Plumtastic' and will be referred to hereafter by its cultivar name, 'Plumtastic'. The new cultivar represents a new moss *phlox*, a herbaceous perennial grown for landscape use.

The new invention arose from an ongoing controlled breeding program conducted by the Inventor in Glencoe, Ill. The objectives of the breeding program are to develop improved cultivars of interspecific *Phlox* hybrids with novel ornamental traits such as unique flower colors, plant habits, flower fragrance and adaptability to garden conditions in the upper Midwest (U.S.D.A. Zone 5) and similar climates.

'Plumtastic' was derived from a cross made in April of 2010 under controlled conditions between *Phlox subulata* 'Fort Hill' (not patented) as the female parent and *Phlox kelseyi* 'Lemhi Midnight' (not patented) as the male parent. The resulting seedlings were planted for evaluation in June of 2011. 'Plumtastic' was selected in May of 2012 as a single unique plant from amongst the resulting seedlings.

Asexual propagation of the new cultivar was first accomplished by shoot tip cuttings by the Inventor in May of 2012 in Glencoe, Ill. Asexual propagation by shoot tip cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'Plumtastic' as a unique cultivar of *Phlox*.

1. 'Plumtastic' exhibits a low dense groundcover habit that is shorter in height than for most *Phlox*.
2. 'Plumtastic' exhibits petals that overlap for one-half to three-quarters of their length.
3. 'Plumtastic' exhibits flowers that emerge light rose pink in color, ageing to a medium and then dark rose to red-violet color.
4. 'Plumtastic' exhibits flowers that emerge with a large, distinct center eye that is white in color and fills with pigment as the flowers age.
5. 'Plumtastic' exhibits small petal striae that form two distinct dark violet lines at the base of each petal lobe and persist for the life of the flower.
6. 'Plumtastic' exhibits flowers that cover 90% of the plant at peak bloom.

The female parent of 'Plumtastic', 'Fort Hill', differs from 'Plumtastic' in having a petal with a more distinct and deep cleft, in having a re-blooming habit, in having flowers that are persistently light rose-pink in color (non-fading), and in having flowers that lack a central eye. The male parent of 'Plumtastic', 'Lemhi Midnight', differs from 'Plumtastic' in having petals that lack striae, in having petals with rounded apices and no cleft, in having flowers that cover 50% or less of the plant at peak bloom, and in having flowers that are persistently deep blue-violet in color (non-fading). 'Plumtastic' can be most closely compared to the *Phlox subulata* cultivar 'Laura' (not patented) and the *Phlox kelseyi* cultivar 'Lemhi Purple' (not patented). 'Laura' is similar to 'Plumtastic' in flower color at anthesis and in having small petal striae that persist for the life of the flower. 'Laura' differs from 'Plumtastic' in having flowers that remain light violet pink for the life of the flower, in having flowers that are smaller in size, in having flower petals that do not overlap, and in having flowers that lack a central eye. 'Lemhi Purple' is similar to 'Plumtastic' in having flowers of a similar size and in having a low, spreading mat-forming plant habit that is short for a *Phlox* moss. 'Lemhi Purple' differs from 'Plumtastic' in having flowers that lack striae, in having flowers with a central eye that is smaller in size, in having narrow petals that do not overlap, and in having flowers that cover 50% or less of the plant at peak bloom.

BRIEF DESCRIPTION OF THE DRAWINGS

The accompanying colored photographs illustrate the overall appearance and distinct characteristics of the new *Phlox*. The photographs were taken of three year-old plants 'Plumtastic' as grown outdoors in a trail garden in Glencoe, Ill.

The photograph in FIG. 1 provides a top view of a plant of 'Plumtastic' in bloom.

Figure 1:
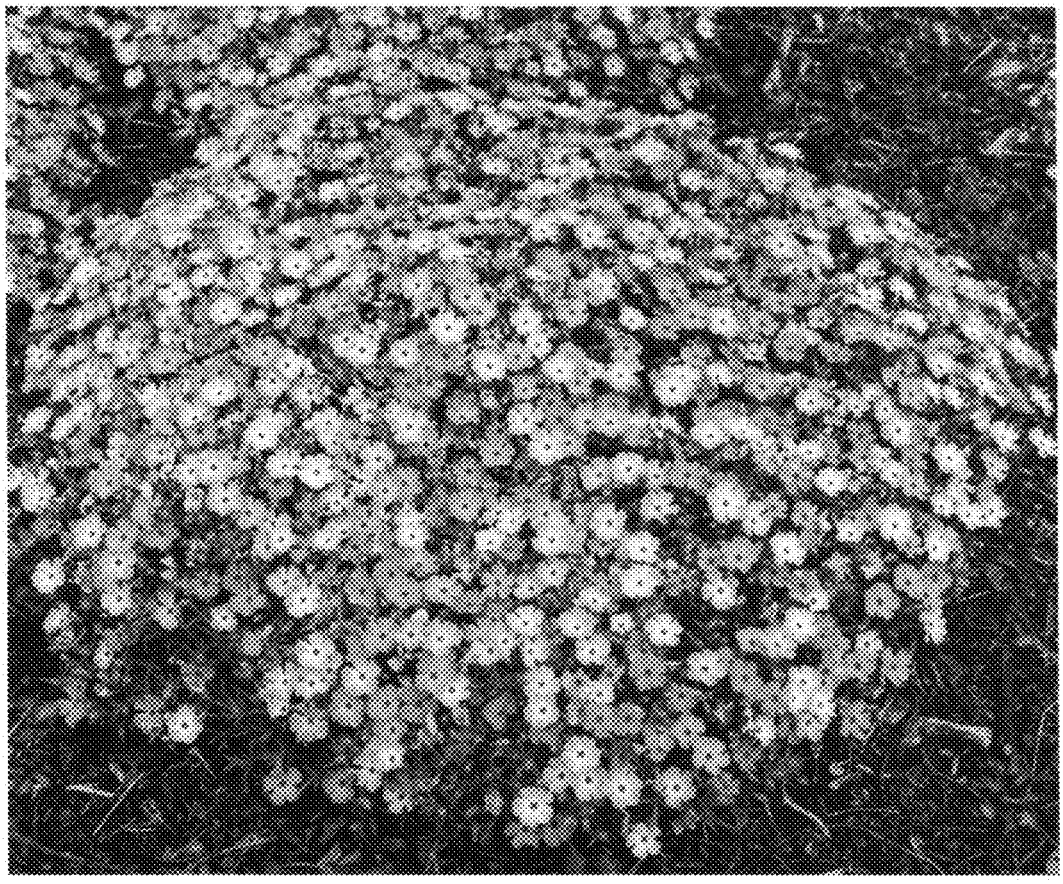
Figure 2:
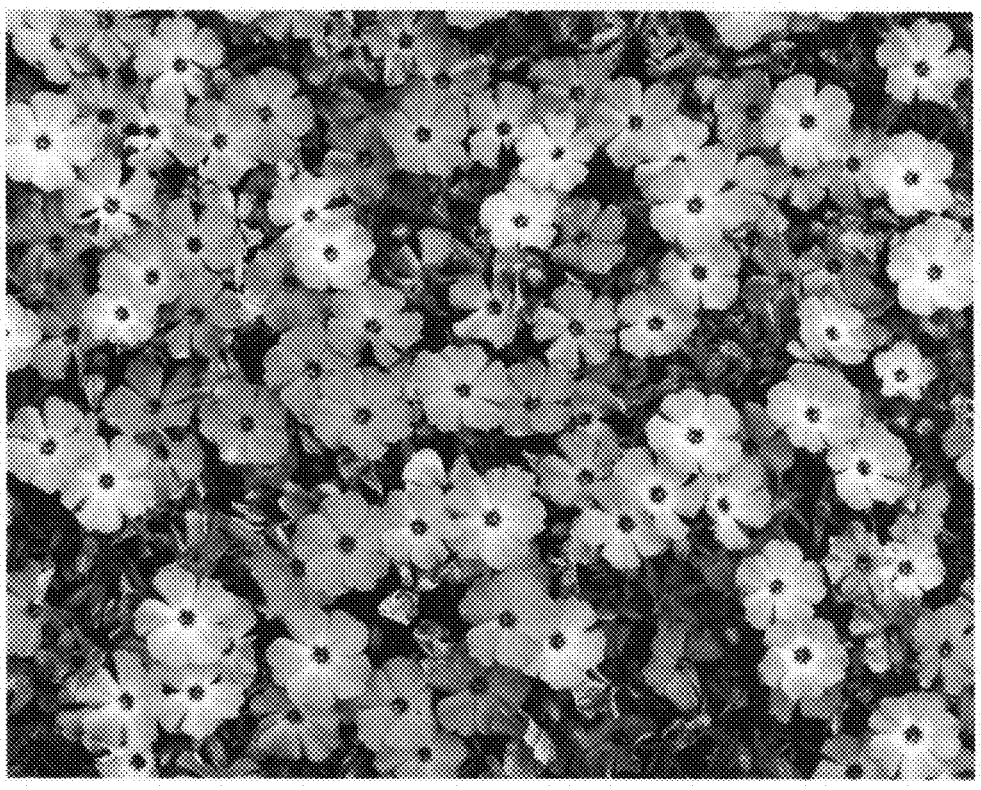

The photograph in FIG. 2 provides a close-up view of the flowers of 'Plumtastic'.

The photograph in FIG. 3 provides a view of the low dense groundcover habit of 'Plumtastic'.

The colors in the photographs are as close as possible with the photographic and printing technology utilized and the color values cited in the Detailed Botanical Description accurately describe the colors of the new *Phlox*.

DETAILED BOTANICAL DESCRIPTION OF THE PLANT

The following is a detailed description of three year-old plants of the new cultivar as grown outdoors in a trial garden in Glencoe, Ill. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Blooms for four to five weeks from late April to late May in northern Illinois.

*Plant type*.—Herbaceous perennial.

*Plant habit*.—Low, dense, spreading groundcover.

*Height and spread*.—An average of 7 cm in height and 31 cm in width.

*Hardiness*.—At least hardy in U.S.D.A. Zones 4 to 8.

*Diseases and pests*.—Resistance to powdery mildew (caused by *Erysiphe cichoracearum*) has been observed.

*Root description*.—Fibrous and NN155C in color.

*Root development*.—Shoot tip cutting will root under mist in four to five weeks in late spring to early summer, rooted cutting will fully root in a 2.5 inch pot in about three months and when tranplanted in fall and overwintered in a 4-inch pot, they will bloom the following spring.

*Growth rate*.—Moderate for a moss *phlox*.

*Propagation*.—Shoot tip cuttings.

Stem description:

*Stem size*.—An average of 13 cm in length and 1 mm in width.

*Stem shape*.—Rounded.

*Stem strength*.—Moderately strong and flexible.

*Stem color*.—Young stems; a blend of 196A and 193A, mature stems; 162A.

*Stem surface*.—Young stems; very slightly glossy, and moderately covered with pubescence, mature stems; dull, dry and paper like and moderately covered with pubescence.

*Stem aspect*.—Held horizontally to descending, drooping and falling downward.

*Internode length*.—An average of 6 mm.

*Branching habit*.—Well branched, an average of 10 main stems growing from base of plant.

Foliage description:

*Leaf shape*.—Lanceolate to linear.

*Leaf division*.—Simple.

*Leaf base*.—Truncate to cuneate.

*Leaf apex*.—Acute.

*Leaf venation*.—Pinnate, inconspicuous, matches leaf color on upper and lower surfaces.

*Leaf margins*.—Entire.

*Leaf attachment*.—Sessile.

*Leaf arrangement*.—Opposite and basal rosettes.

*Leaf surface*.—Both surfaces slightly glossy, margins and base moderately covered with pubescence.

*Leaf texture*.—Thick and slightly rubbery.

*Leaf color*.—Upper and lower surface; 139C.

*Leaf size*.—An average of 1.5 cm in length and 2 mm in width.

*Leaf quantity*.—Average per main branch 9 cm in length; average of 9 basal rosettes, 40 leaves per rosette, a total average of 360 leaves per main stem.

*Leaf fragrance*.—Fresh grass-like scent.

Flower description:

*Inflorescence type*.—Panicle on terminus of lateral branches.

*Lastingness of inflorescence*.—About 3 to 4 weeks from the opening of the first flower to senescence of last flower, individual flower lasts about 4-5 days.

*Inflorescence size*.—An average of 4 cm in height and 5 cm in diameter.

*Flower fragrance*.—None detected.

*Flower number*.—An average of 5 per inflorescence.

*Flower aspect*.—Upright and outward from stem, upright from pedicel.

*Flower bud*.—Ovate in shape with broadly acute apex, an average of 1.6 cm in length and 3 mm in width, color; N78B to N78C.

*Flower form*.—Salverform.

*Flower size*.—An average of 1.6 cm in height and 2.1 cm in diameter.

*Corolla tube*.—An average of 1.5 cm in length and 3 mm in width (apex), color a blend of 75A and 75D both surfaces, glabrous and satiny surface on both surfaces.

*Corolla lobes*.—5 petals, obcordate in shape, held nearly horizontally when fully open, overlapping for one-half to three quarters of length, slightly wavy in aspect, an average of 1 cm in length and 7 mm in width, apex rounded and slightly bifid with a broad shallow cleft, base broadly cuneate and fused to tube, entire margins; color upper surface when first open a blend between N75A to N75B with a large central eye N155B and with small striations at the base N88A; as the petals age color transitions to N80A to N80C with small striations a blend between N87A and N88A, as petals near senescence color can transition to as dark as N81A; the large central eye fills with the same pigmentation as the rest of the petal surface by day three; the lower surface when opening and fully open is a blend of N78C to N78D with a small striations of N77A at base; glabrous and slightly satiny on upper and lower surfaces.

*Calyx*.—Campanulate in form, comprised of fused sepals with linear shaped sepal tips free, an average of 1 cm in length and 3 mm in width.

*Sepals*.—5, primarily fused with free tips, linear in shape, entire margins, fused base (about 75%), aristulate apex, an average of 6 mm in length and 1 mm in width, color on inner and outer surface 145C, inner surface; glabrous, smooth, and shiny, outer surface; moderately covered with pubescence.

*Peduncles*.—Rounded in shape, an average of 2 cm in length and 1 mm in width, held upright to outward, moderate in strength, color; 145A to 145C, surface satiny and moderately covered with pubescence.

*Pedicels*.—Rounded in shape, an average of 1.5 cm in length and 1 mm in width, held upright to outward, moderate in strength, color; 145C, surface satiny and moderatelycovered with pubescence.

Reproductive organs:

*Gynoecium*.—1 pistil, stigma; tri-lobed, each lobe is about 1 mm in length and N144A in color, style; about 0.9 cm in length and 0.3 mm in width, N144A in color, ovary; superior, ovate to oval in shape, about 2 mm in length and width, 141C in color.

*Androcoecium*.—5 stamens, anthers; dorsifixed, oblong in shape, 1.3 mm in length, and 23A in color, filaments; adnate to petals, an average of 5 mm in length and 155C in color, pollen is abundant in quantity and 23A in color.

*Seeds*.—None observed.

It is claimed:

1. A new and distinct cultivar of *Phlox* plant named 'Plumtastic' as herein illustrated and described.

* * * * *